(12) United States Patent
Galliani et al.

(10) Patent No.: US 7,645,798 B2
(45) Date of Patent: Jan. 12, 2010

(54) N-(2-HYDROXYALKANOYL)-N,N'-DIALKYLUREAS AND A PROCESS FOR THEIR PREPARATION

(75) Inventors: Guido Galliani, Desio-Milano (IT); Marco Orlandi, Milan (IT); Bruno Rindone, Segrate-Milano (IT); Alberto Terraneo, Meda-Milano (IT)

(73) Assignee: CHORISIS S.r.l., Mariano Cornense, Como (IT)

( * ) Notice: Subject to any disclaimer, the term of this patent is extended or adjusted under 35 U.S.C. 154(b) by 0 days.

(21) Appl. No.: 11/985,935

(22) Filed: Nov. 19, 2007

(65) Prior Publication Data

US 2008/0085937 A1 Apr. 10, 2008

Related U.S. Application Data

(63) Continuation of application No. PCT/EP2006/004674, filed on May 17, 2006.

(51) Int. Cl.
*A61K 31/17* (2006.01)
*C07D 263/00* (2006.01)

(52) U.S. Cl. .................. 514/594; 514/588; 548/226; 564/44

(58) Field of Classification Search ............... 548/226; 564/44; 514/594, 588; 525/514, 528
See application file for complete search history.

(56) References Cited

FOREIGN PATENT DOCUMENTS

DE 836352 * 4/1952

OTHER PUBLICATIONS

Rekker Roelof Feike, Mehod of preparing oxazolidin-2, 4-dion-descendants, 1949, Deutsches Patentamt, English translation, 4 pages.*

Geffken, Archiv, der Pharmazie, vol. 313, No. 10, (1980) pp. 817-825.
Shapiro et al., JACS, vol. 81,(1959) pp. 6498-6504.
Clarke-Lewis, 2,4-Oxazolidinediones, Chemical Reviews, vol. 58, (1958) pp. 63-99.

* cited by examiner

*Primary Examiner*—Porfirio Nazario-Gonzalez
*Assistant Examiner*—Yate' K Cutliff
(74) *Attorney, Agent, or Firm*—James V. Costigan; Hedman & Costigan, P.C.

(57) ABSTRACT

N-(2-hydroxyalkanoyl)-N,N'-dialkylureas of general formula (1) are described $$A\text{-}X\text{-}(A)_m \quad (1)$$

where A:

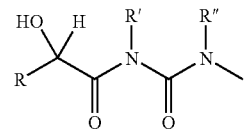

m=0 or m=1; when m=0, X=R''', where R''' is an aliphatic, cycloaliphatic, arylaliphatic radical, $C_1$-$C_{18}$; when m=1, X=—$(CH_2)_n$—, where n is an integer from 1 and 20, preferably from 2 to 6;

R is chosen among H, and alkyl radicals $C_1$-$C_8$, possibly substituted with halogen atoms; R' is an aliphatic, cycloaliphatic, arylaliphatic radical, $C_1$-$C_{18}$; R'' is chosen among H, aliphatic, cycloaliphatic, arylaliphatic radical, $C_1$-$C_{18}$.

The preparation of said compounds is described, as well as the preparation of corresponding polymers.

14 Claims, No Drawings

N-(2-HYDROXYALKANOYL)-N,N'-DIALKYLUREAS AND A PROCESS FOR THEIR PREPARATION

This application is a continuation-in-part of PCT/EP2006/004674, filed Nov. 17, 2006.

The present invention describes N-(2-hydroxyalkanoyl)-N,N'-dialkylureas and the procedure to obtain them.

3-alkyloxazolidin-2,4-diones are heterocylic compounds described in an old review (J. M. Clark-Lewis, "2,4-oxazolidinediones", Chem. Rev., 58, 63-99, 1958). This paper describes methods of preparation, reactivity, and possible uses. However, data on the reactivity of oxazolidine-2,4-diones are scarce, being limited to the description of hydrolysis and a few other reactions.

A new method to prepare 3-alkyloxazolidin-2,4-diones and 3,3'-alkylen-bis-3-oxazolidine-2,4-diones is described in Italian patent application Serial No. MI2005A00892, filed May 17, 2005, which is incorporated by reference. Such a preparation is based on the reaction of cyclic carbonates with either a monoamine or with a primary diamine, both of which can be aliphatic, cycloaliphatic, or arylaliphatic, followed by the oxidation of the adduct thus obtained with an oxidizing agent, preferably with pyridinium chlorochromate.

Surprisingly, we have found that the reaction of 3-alkyloxazolidin-2,4-diones with either primary or secondary amines (or diamines) yields N-(2-hydroxyalkanoyl)-N,N'-dialkylureas.

In agreement with that, the presents invention is related with compounds of general formula (1)

Where A=

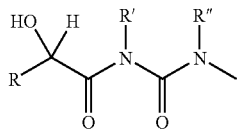

m=either 0, or 1;

when m=0, then X=R''', where R''' is an aliphatic, cycloaliphatic, arylaliphatic radical, $C_1$-$C_{18}$;

when m=1, then X=—$(CH_2)_n$—, where n is comprised between 1 and 20, preferably between 2 and 6;

R is chosen among H and alkyl radicals $C_1$-$C_8$, possibly substituted with halogen atoms;

R' is an aliphatic, cycloaliphatic, arylaliphatic radical, $C_1$-$C_{18}$;

R'' is chosen among hydrogen or an aliphatic, cycloaliphatic, arylaliphatic radical, $C_1$-$C_{18}$.

Typical examples of compounds corresponding to the general formula (1), when m=0, are the compounds of general formula (2)

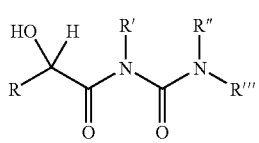

which can be defined as N-(2-hydroxyalcanoyl)-N,N'-dialkylureas. When R=methyl and R'''=H, compounds of general formula (2) can be classified as N-lactyl-N,N'-dialkylureas. Typical examples of compounds of general formula (2), whose preparation is described in the experimental part, are:

Compound (2)1 of general formula (2), where R=methyl; R'=R''=n-pentyl; R'''=H;

Compound (2)2 of general formula (2) where R=methyl; R'=n-pentyl; R''=benzyl; R'''=H;

Compound (2)3 of general formula (2) where R=methyl; R'=n-pentyl; R''=cyclohexyl; R'''=H;

Compound (2)4 of general formula (2) where R=methyl; R'=cyclohexyl; R''=n-pentyl; R'''=H;

Compound (2)5 of general formula (2) where R=methyl; R'=cyclohexyl; R''=benzyl; R'''=H;

Compound (2)6 of general formula (2) where R=methyl; R'=R''=cyclohexyl; R'''=H;

Compound (2)7 of general formula (2) where R=methyl; R'=benzyl; R''=n-pentyl; R'''=H;

Compound (2)8 of general formula (2) where R=methyl; R'=R''=benzyl; R'''=H.

Typical examples of compound of general formula (1) when m=1 are the compounds of general formula (3)

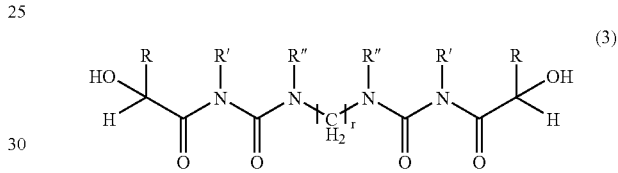

which can be classified as bis-(N-(2-hydroxyalcanoyl)-N,N'-dialkyl-N'-alkylene)-ureas. When R=methyl and R''=H, compounds of general formula (3) can be classified as bis-(N-lactyl-N-alkyl-N'-alkylene)-ureas. In the case of N-lactyl-N,N'-dialkylureas, reaction occurs between 3-alkyl-5-methyloxazolidine-2,4-diones and a primary monoamine according to scheme (1)

SCHEME 1

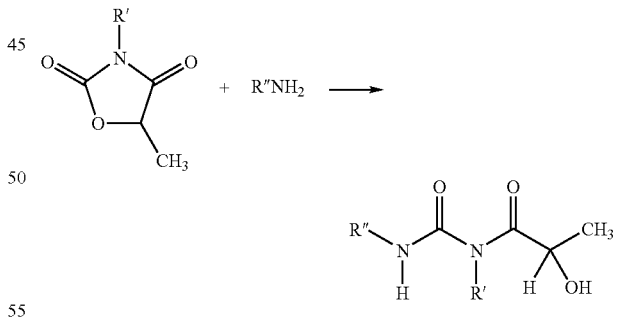

In the case of bis-(N-lactyl-N-alkyl-N'-alkylene)-ureas, reaction occurs between two molecules of 3-alkyl-5-methyloxazolidine-2,4-diones and an aliphatic diamine. These N-lactyl-N,N'-dialkylureas and bis-N-lactyl-N,N'-dialkylureas are stable compounds, in some cases crystalline compounds.

Moreover, this invention describes a procedure to prepare compound of general formula (1), which includes the reaction of 3-alkyloxazolidine-2,4-diones with a mono- or diamine at a temperature from 50° C. to 140° C., preferably from 80° C. to 120° C.

In the preferred way to perform the reaction, the molar ratio between 3-alkyloxazolidine-2,4-diones and the mono- or diamine is nearly 1:1 in the case of monoamines and 2:1 in the case of diamines. However, it is possible to use different molar ratios, even though this implies a more complex purification of the reaction products.

The process described by this invention is preferably performed without any solvent, with a considerable advantage to avoid recovering and recycling solvents. N-lactyl-N,N'-dialkylureas represent useful intermediates to prepare new molecules, particularly in pharmaceutical development, with a special interest for peptidomimetics drugs.

The present invention describes products of general formula (4) as well

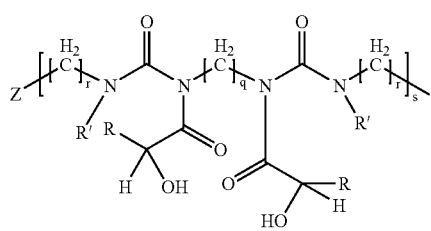

(4)

where Z is chosen between radicals (5) and (6)

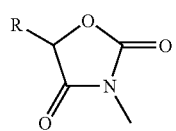

(5)

—NHR'

(6)

R is chosen among H and alkyl radicals $C_1$-$C_8$, possibly substituted with halogen atoms;
R' is either hydrogen or alkyl;
q can range from 1 to 20, preferably from 2 to 8;
r can range from 1 to 20, preferably from 2 to 8;
s is any integer number.

The aforementioned products of general formula (4) are polymeric products, namely poly-N-(2-hydroxyalkafloyl)-N-alkylidene-N'-alkylidefle-N'-alkylidene-ureas, which can be obtained by reacting 3,3'-alkylidene-bis-oxazolidine-2,4-diones with diamines. Typical compounds that represent these kinds of compounds are poly-N-lactyl-N-alkylidene-N'-alkylideneuteas, where R=methyl. Compounds of this kind are a new class of polymers, which can be used for examples, when terminal groups are amino groups, as prepolymers to be further polymerized in order to obtain traditional polymers as polyurethanes and polyureas with a larger degree of crystallinity. polyureas are well known polymers, whose industrial application is widespread in many technologies. It is also very well known to the person skilled in the art that unfortunately common commercial polyureas cannot be functionalized, although this would be highly desirable. The invention of these pre-polymers represents a solution to the crucial technical problem of combining the properties of polyureas with the need of a functionalization of the polymer chain. By a proper choice of the bis-oxcazolidinediones to be coupled with difunctional amines, structural, mechanical, and rheological properties of polyureas can be conveniently modulated. Functionalization of polyurea, for instance, would allow to prepare improved chromatographic resins.

Moreover, in the case of lactylpolyureas, the lactyl group represents a usual point of attack for microorganisms, which makes this kind of polymer more prone to biodegradation as it is well known to the experts of the field.

The separation of levonorgestrel has been carried out, first using a column with a stationary phase consisting of non functionalized aminopropylsilica and using hexane/ethyl acetate 2/1 as eluent.

The same separation has been repeated using the same eluent and, as stationary phase, aminopropylsilica functionalized with an oligomer within the scope of compound (4) wherein Z is formula (5), r and q are equal to 2 and s is equal to 3, R and R' are hydrogen. The functionalization is carried out by thermally treating the aminopropylsilica with the oligomer as disclosed in the example of the application in re and then by thermally capping the so obtained product with benzyl amine, in a solvent free environment.

The column with the stationary phase consisting of functionalized silica has a number of theoretical plates equal to 1.2 with respect to the number of theoretical plates of the column with the stationary phase of non functionalized silica, such datum representing the resolution capacity of the column, which is therefore higher for the solution according to the present application.

Further the column with the stationary phase consisting of functionalised silica has a charge capacity equal to 1.5 with respect to the charge capacity of the column with the stationary phase of non functionalized silica. Polymers are prepared by reacting blocks of polyurethane prepolymers bearing terminal amino groups and blocks of poly-N-lactylurea prepolymers bearing terminal oxazolidinedione groups. The resulting polymers are mixed poly-N-lactylureas-polyurethanes showing higher resistance to high temperatures. The elastomeric properties of polymers based on poly-N-lactylureas prepolymers are maintained.

Polyureas at high molecular weight are prepared by reacting blocks of polyurea prepolymers bearing terminal amino groups with low molecular weight poly-N-lactylurea prepolymers bearing terminal oxazolidinedione groups. Also in this case, thermal resistance is improved as to usual polyureas.

Low molecular poly-N-lactylurea polymers bearing terminal oxazolidinedione groups are reacted with aminopropyl silica. Products thus obtained are thermally cured with an aliphatic amine to react all of unreacted oxazolidinedione groups. Materials thus obtained are useful as chromatographic stationary phases for both analytical and preparative purposes.

Materials of formula 4 are partially or totally acylated at the lactyl hydroxyl with several acyl chlorides. Chromatographic properties are improved as to the loading capacity of the material.

The following examples are reported to better understand the present invention.

EXAMPLES

Examples 1-8

Preparation of Compounds (2)1-(2)8

20 mmoles of 3-alkyl-5-methyloxazolidine-2,4-dione and 20 mmoles of amine are mixed in a reaction vessel under nitrogen. The mixture is stirred at 100° C. for 16 hours, cooled at room temperature, and purified in a silica gel column, eluting with a mixture of dichloromethane and ethyl acetate (ratio 3:1). Reaction and purification are followed by GC-MS. Stoicheiometric yields of N-lactyl-N,N'-dialkylureas (formula 2) are reported in Table 1. The only products obtained in addition to N-lactyl-N,N'-dialkylureas are starting products. All reaction products are characterized by these IR bands: 3300 cm$^{-1}$, 1720 cm$^{-1}$, as a shoulder, 1680 cm$^{-1}$, 1650 cm$^{-1}$. Reaction products were characterized by GC-MS and NMR, both $^1$H and $^{13}$C (samples dissolved in d$_6$-DMSO). Data referred to the examples of Table 1 are here reported:

(2)-1:
MS: 272, M$^+$ (0.6%), 186 (9.8%), 159 (27.6%), 144 (7.4%), 130 (55.8%), 114 (100.0%), 98 (64.4%), 85 (28.2%), 71 (84.0%), 56 (42.9%);
$^1$H-NMR: (chemical shifts reported in δ units) 7.7 (t, 1H), 7.1 (t, 1H), 4.8 (qd, 1H), 3.0 (m, 2H), 2.9 (m, 2H), 1.4 (dd, 3H), 1.2 (m, 12H), 0.8 (m, 6H);
$^{13}$C-NMR: 170 (C=O), 154 (C=O), 69 (1H), 40 (2H), 38 (2H), 31 (6C, 2H), 22 (3H), 18 (3H), 14 (3H).

(2)-2:
MS: 292, M$^+$, (0.5%), 206 (2.5%), 179 (16.7%), 161 (32.0%), 133 (17.3%), 106 (31.5%), 91 (100.0%);
$^1$H-NMR: 8.4 (t, 1H), 7.4-7.2 (m, 5+1H), 4.9 (qd, 1H), 4.3 (d, 2H), 2.9 (m, 2H), 1.4 (dd, 2H), 1.3 (dd, 3H), 1.2 (m, 4H), 0.8 (td, 3H);
$^{13}$C-NMR: 170 (C=O), 155 (C=O), 139 (Ar), 128 (2C, Ar), 126 (2+1C, Ar), 69 (1H), 42 (2H), 40 (2H), 28 (2H), 27 (2H), 22 (2H), 18 (3H), 13 (3H)
Melting point: 76.7° C.

(2)-3:
MS: 284, M$^+$ (0.5%), 203 (16.3%), 186 (42.4%), 171 (6.5%), 159 (54.3%), 142 (4.3%), 130 (100.0%), 114 (39.1%), 102 (18.5%);
$^1$H-NMR: 7.8 (d, 1H), 7.3 (t, 1H), 4.9 (qd, 1H), 3.6 (m, 1H), 2.9 (m, 2H), 1.8 (dd, 3H), 1.7-1.0 (m, 16H), 0.8 (td, 3H);
$^{13}$C-NMR: 168 (C=O), 155 (C=O), 69 (1H), 47 (1H), 40 (2H), 32 (2C, 2H), 29 (2H), 28 (2H), 25 (2H), 24 (2C, 2H), 22 (2H), 18 (3H), 14 (3H)

(2)-4:
MS: 284, M$^+$ (0.4%), 198 (14.7%), 171 (34.1%), 159 (21.6%), 142 (100.0%), 126 (22.7%), 114 (36.4%), 98 (12.5%), 83 (43.2%).
$^1$H-NMR: 7.8 (t, 1H), 7.1 (d, 1H), 4.8 (qd, 1H), 3.2 (m, 1H), 3.0 (m, 2H), 1.7 (dd, 3H), 1.5-1.0 (m, 16H), 0.8 (td, 3H)
$^{13}$C-NMR: 170 (C=O), 156 (C=O), 69 (1H), 49 (1H), 38 (2H), 32 (2C, 2H), 25 (2H), 24, (2C, 2H), 23 (2H), 22 (2H), 20 (2H), 18 (3H), 14 (3H)

(2)-5:
MS: 305 (M$^+$+1, 0.3%), 179 (15.4%), 161 (100.0%), 142 (34.5%), 133 (41.7%), 106 (43.4%), 91 (85.7%).
$^1$H-NMR: 8.4 (t, 1H), 7.1-7.3 (m, 5+1H), 4.9 (qd, 1H) 4.3 (s, 2H), 3.2 (m, 1H), 1.0-1.7 (m, 10H), 1.3 (d, 3H).
$^{13}$C-NMR: 171 (C=O), 154 (C=O), 139 (Ar), 128 (2C, Ar), 126 (2+1C, Ar), 65 (1H), 49 (1H), 42 (2H), 33 (2H), (2C, 2H), 24 (2C, 2H), 18 (3H).

(2)-6:
MS: 296 (M$^+$, 0.3%), 215 (3.8%), 207 (4.7%), 198 (11.3%), 171 (38.7%), 153 (3.8%), 142 (50.0%), 126 (21.7%), 97 (56.6%), 83 (100.0%);
$^1$H-NMR: 7.6 (d, 1H), 7.2 (d, 1H), 4.8 (q, 1H), 3.5 (m, 1H), 3.2 (m, 1H), 1.1-1.8 (m, 20H), 1.2 (d, 1H);
$^{13}$C-NMR: 169 (C=O), 154 (C=O), 69 (1H), 49 (1H), 47 (1H), 33 (2C, 2H), 25 (4C, 2H), 24 (4C, 2H), 18 (3H)
Melting point: 164.8° C.

(2)-7:
MS: 292 (M$^+$, 0.2%), 179 (10.1%), 161 (37.7%), 150 (8.7%), 133 (43.5%), 118 (3.7%), 106 (26.1%), 91 (100.0%);
$^1$H-NMR: 7.8 (t, 1H), 7.7 (t, 1H), 7.2-7.3 (m, 5H), 4.8 (qd, 1H), 4.2 (s, 2H), 3.0 (m, 2H), 1.4 (t, 2H), 1.3 (m, 6H), 0.8 (t, 3H);
$^{13}$C-NMR: 170 (C=O), 155 (C=O), 139 (Ar), 129 (2C, Ar), 127 (2+1C, Ar), 69 (1H), 44 (2H), 39 (2H), 29 (2C, 2H), 22 (2H), 18 (3H), 14 (3H);
Melting point: 68.7° C.

(2)-8:
MS: 206 (M$^+$+1-benzylamine, 7.5%), 179 (13.9%), 159 (6.9%), 150 (47.2%), 133 (44.4%), 114 (22.0%), 105 (26.4%), 91 (100.0%);
$^1$H-NMR: 8.5 (t, 1H), 7.8 (t, 1H), 7.2-7.3 (m, 10H), 4.9 (qd, 1H), 4.3 (s, 2H), 4.2 (s, 2H), 1.4 (d, 3H);
$^{13}$C-NMR: 170 (C=O), 155 (C=O), 139 (2C, Ar), 128 (4C, Ar), 127 (4+2C, Ar), 70 (1H), 44 (2H), 42 (2H), 18 (3H);
Melting point: 93.8° C.

Example 9

Preparation of a Poly-N-Lactyl-N-hexamethylene-N'-hexamethyleneurea

The first step of this preparation is the synthesis of 3,3'-hexamethylene-bis-(5-methyloxazolidine-2,4-dione). 10 moles of hexamethylenediamine and 20 mmoles of propylene carbonate are mixed and maintained at 60° C. for two hours. The adducts mixture thus formed is cooled and dissolved in 120 ml of methylene chloride, then treated at room temperature with 120 mmoles of pyridinium chlorochromate. The mixture is stirred for two hours at room temperature. The liquid is separated from the tarry residue and concentrated under reduced pressure. The residue is eluted with methylene chloride on a silica gel column. Fractions containing the product corresponding to formula 3, as detected by GC-MS and identified by .sup.1H and $_{13}$C-NMR, are collected and dried.

MS: 312 (M$^+$, 7.5%), 241 (7.9%), 184 (37.4%), 170 (12.6%), 156 (5.6%), 143 (7.0%), 129 (3.3%), 116 (100.0%), 82 (44.9%);
$^1$H-NMR: 5.1 (q, 2H), 3.4 (m, 4H), 1.6 (m, 4H), 1.5 (d, 6H), 1.3 (m, 4H);
$^{13}$C-NMR: 174 (C=O), 156 (C=O), 76 (1H), 40 (2H), 27 (2H), 26 (2H), 16 (3H).

The product, 3,3'-hexamethylene-bis-(5-methyloxazolidine-2,4-dione) thus prepared is reacted with hexamethylenediamine, in a molar ratio 1.2:1 (amine/oxazolidinedione). The reaction is performed without any solvent, by heating the mixture at 120° C. and then raising temperature till the product solidifies. A glassy polymer is formed, with a high melting point.

IR (film): 3320 cm$^{-1}$ (broad), 2930 cm$^{-1}$, 2860 cm$^{-1}$, 1730 cm$^{-1}$, 1650 cm$^{-1}$ (broad), 1520 cm$^{-1}$ (broad), 1250 cm$^{-1}$ (broad), 780 cm$^{-1}$; PST (polymer stick temperature): 150-155° C.

TABLE 1

| Example | (1) where R= | Amine | Product (2) R= | Product (2) R'= | Yield (%) |
|---|---|---|---|---|---|
| 1 | n-pentyl | n-pentylamine | n-pentyl | n-pentyl | 85 |
| 2 | n-pentyl | benzylamine | n-pentyl | benzyl | 83 |
| 3 | n-pentyl | cyclohexylamine | n-pentyl | cyclohexyl | 59 |
| 4 | cyclohexyl | n-pentylamine | cyclohexyl | n-pentyl | 73 |
| 5 | cyclohexyl | benzylamine | cyclohexyl | benzyl | 59 |
| 6 | cyclohexyl | cyclohexylamine | cyclohexyl | cyclohexyl | 55 |
| 7 | benzyl | n-pentylamine | benzyl | n-pentyl | 78 |
| 8 | benzyl | benzylamine | benzyl | benzyl | 62 |

The invention claimed is:

1. A compound of general formula (1)

A-X-(A)$_m$ wherein A=

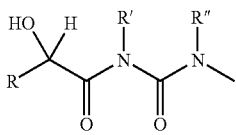

m=0 or 1;

when m=0, X=R''', where R''' is an aliphatic, cycloaliphatic, or arylaliphatic radical having $C_1$-$C_{18}$;

when m=1, X=—(CH$_2$)$_n$—, where n is an integer comprised between 1 and 20;

R is chosen among H and alkyl radicals $C_1$-$C_8$, possibly substituted with halogen atoms;

R' is an aliphatic, cycloaliphatic, or arylaliphatic radical, having $C_1$-$C_{18}$;

R'' is chosen among H, aliphatic, cycloaliphatic, or arylaliphatic radical having $C_1$-$C_{18}$.

2. The compound according to claim 1, where R''=H.

3. The compound according to claim 1, wherein, when m=0, being R' and R''' equal or different, R' and R''' are chosen among alkyl, cycloalkyl, benzyl radicals, bearing 1 to 18 carbon atoms.

4. The compound according to claim 1, wherein m=1, X=—(CH$_2$)$_n$— with n from 2 to 6.

5. The compound according to claim 1, wherein R is CH$_3$.

6. The compound according to claim 1, wherein m=0, R=methyl; R'''=H and where:

(a) R'=R''=n-pentyl;
(b) R'=n-pentyl; R''=benzyl;
(c) R'=n-pentyl; R''=cyclohexyl;
(d) R'=cyclohexyl; R''=n-pentyl;
(e) R'=cyclohexyl; R''=benzyl;
(f) R'=R''=cyclohexyl;
(g) R'=benzyl; R''=n-pentyl;
(h) R'=R''=benzyl.

7. The compound according to claim 1 with m=1, of general formula (3).

8. Procedure for preparing compound of general formula (1), including the reaction of 3-alkyloxazolidine-2,4-diones with a mono- or diamine at a temperature between 50° C. and 140° C.

9. Procedure according to claim 8, wherein temperature is between 80° C. and 120° C.

10. Procedure according to claim 8, wherein the molar ratio between 3-alkyloxazolidine-2,4-diones and mono- or diamine is nearly 1:1 for monoamines and 2:1 for diamines.

11. Procedure according to claim 8, characterized by performing the reaction without any solvent.

12. A compound of general formula (4)

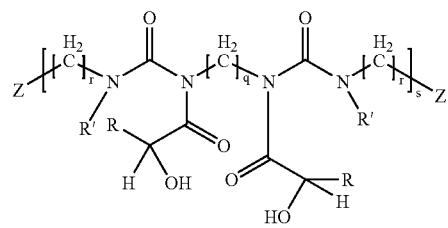

(4)

wherein Z is chosen between radicals (5) and (6):

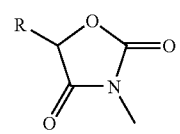

(5)

—NHR'    (6)

R is chosen among H and alkyl radicals $C_1$-$C_8$, possibly substituted with halogen atoms;

R' is either H or alkyl;

q is an integer between 1 and 20;

r is an integer between 1 and 20;

s is any integer.

13. The compound according to claim 12, wherein "q" is an integer between 2 and 8, and "r" is an integer from 2 to 8.

14. The compounds according to claim 1 where n is between 2 and 6.

* * * * *